US006311567B1

(12) United States Patent
England

(10) Patent No.: US 6,311,567 B1
(45) Date of Patent: Nov. 6, 2001

(54) AUTOMATIC STATIC LOAD TESTING FOR PILES

(75) Inventor: Melvin England, Middlesex (GB)

(73) Assignee: Kvaerner Cementation Foundation Ltd., Rickmansworth Herts (GB)

( * ) Notice: Subject to any disclaimer, the term of this patent is extended or adjusted under 35 U.S.C. 154(b) by 0 days.

(21) Appl. No.: 09/380,984

(22) PCT Filed: Mar. 12, 1998

(86) PCT No.: PCT/GB98/00750

§ 371 Date: Feb. 16, 2000

§ 102(e) Date: Feb. 16, 2000

(87) PCT Pub. No.: WO98/41696

PCT Pub. Date: Sep. 24, 1998

(30) Foreign Application Priority Data

Mar. 14, 1997 (GB) .................................................. 9705311

(51) Int. Cl.[7] ........................................................ G01N 3/00
(52) U.S. Cl. ................................................. 73/806; 73/803
(58) Field of Search .............................. 73/788, 803, 805, 73/806, 818

(56) References Cited

U.S. PATENT DOCUMENTS

| 3,948,091 | * | 4/1976 | Voll ........................................ 73/806 |
| 5,325,702 | | 7/1994 | Verstraeten . |
| 5,511,431 | | 4/1996 | Hinton . |
| 5,699,274 | * | 12/1997 | Starostovic, Jr. ..................... 702/113 |
| 6,053,052 | * | 4/2000 | Starostovic .............................. 73/851 |

FOREIGN PATENT DOCUMENTS

| 1214474 | 12/1970 | (GB) . |
| 2071267 | 9/1981 | (GB) . |
| 2157457 | 10/1985 | (GB) . |
| 2163870 | 3/1986 | (GB) . |
| 2284673 | 6/1995 | (GB) . |
| 2205959 | 12/1998 | (GB) . |

OTHER PUBLICATIONS

England et al., "Review of foundation testing methods and procedures", *Proc. Istn Civ. Engrs Geotech. Engng.* vol. 107, pp. 135–142, (1994).

England, "New Techniques for Reliable Pile Installation and Pile Behavior Design Analysis", *Transportation Research Record*, vol. 1447, pp. 39–48, (1994).

The Patent Office, Derwent Info Ltd., SU 861476.

Precision Monitoring & Control Ltd., "Method Statement for Static Pile Load Testing Using Electronic Data Logging Equipment", (1992).

* cited by examiner

*Primary Examiner*—Max Noori
(74) *Attorney, Agent, or Firm*—Browdy and Neimark

(57) ABSTRACT

There is disclosed a method and apparatus for testing the static load-bearing capacity of a pile, wherein a test load is applied to the top of the pile (2) by way of a jack (1) braced against a reaction member (3) and the magnitude of the test load and the resulting displacement of the pile are measured and communicated to an electronic computer (7). The electronic computer (7) issues control signals to the jack (1) in response to the measured magnitude of the test load so as to apply a predetermined regime of test loads to the top of the pile (2). By automatically monitoring the applied test load, it is possible to maintain a desired load with a high level of accuracy for an extended period of time without the need for operator intervention.

16 Claims, 3 Drawing Sheets

AUTOMATIC STATIC LOAD TESTING FOR PILES

CROSS REFERENCE TO RELATED APPLICATION

The present application is the national stage under 35 U.S.C. 371 of PCT/GB98/00750, filed Mar. 12, 1998.

The present invention relates to a method and apparatus for testing the static load-bearing capacity of engineering piles.

Piles, usually made out of concrete, are generally used to form the foundations of buildings or other large structures. Before using the piles as a Foundation for further building work, it is important to test the static load-bearing capacity of each pile. This is generally done by applying a test load to the top of a pile by way of a hydraulic jack braced against a reaction system comprising a cross-beam which is anchored in place at its ends. The test load is generally measured by monitoring the hydraulic pressure supplied to the jack, and the associated displacement of the pile is measured by using a displacement sensor. Frequently, the displacement of the pile is measured for a number of increasing test loads, each applied for a predetermined time. Because the applied test loads tend to be high, there is a significant danger to operating personnel should the cross-beam or its anchorages fail, particularly if the operating personnel are required to read test values from a gauges located on equipment located close to the top of the pile.

Furthermore, because the applied test load has to be maintained and adjusted by operating the jack manually, it is necessary for operating personnel to be in attendance at all times. It is not safe for a single operator to work alone, particularly overnight (the typical time taken to perform a comprehensive static load test can often be as much as 18 hours), and accordingly the present method of static load testing is expensive, as well as being slow.

Another disadvantage of the known static load-testing equipment is that the quality of the data obtained is not always consistently good. Typical data required from a static load test are the record of displacement of the pile head and the load applied. Although manual reading and recording of the dial gauges employed in a static load test should not present an insurmountable difficulty in terms of accuracy and regularity, it is the application of the load that generally is the source of poor quality data. This is principally due to the need to attend continuously to a manual hydraulic pump in order to maintain the load with any degree of constancy. A further source of error arises through the use of a pressure gauge to derive the applied test load by way of calibration charts. The accuracy with which the load can be maintained is governed by the resolution with which the gauge can be read. Assuming the operator performing the load control is entirely dedicated and doing his utmost to maintain the load, he may at best be able to read a pressure or load column gauge to 1%. This implies that the load variation is not likely to be better than around ±2%. This in turn means that the pile head displacement recording of a pile whose elastic shortening alone is, say, 5 mm, will fluctuate by ±0.1 mm according to this load variation.

According to a first aspect of the present invention, there is provided a method of testing the static load-bearing capacity of a pile, wherein:

i) a test load is applied to the top of the pile by way of a jack braced against a reaction member;

ii) the magnitude of the test load is determined by measuring means and communicated to an electronic computer;

iii) the resulting displacement of the pile is measured by at least one displacement sensor and communicated to said electronic computer; characterised in that:

iv) the electronic computer issues control signals to the jack in response to the measured magnitude of the test load so as to keep the test load substantially constant;

v) the electronic computer determines when a definite settlement rate for the pile has been attained and then issues control signals to the jack no as to apply a new test load of different magnitude to the top of the pile in accordance with a predetermined regime of test loads; and vi) steps ii) to v) are repeated until the test regime is completed.

According to a second aspect of the present invention, there is provided an apparatus for testing the static load-bearing capacity of a pile, the apparatus comprising:

i) an electronic computer with a power supply;

ii) a jack, which in use is braced between the pile and a reaction member so as to apply a test load to the top of the pile;

iii) means for measuring the magnitude of the test load and communicating this to the computer;

iv) at least one displacement sensor for measuring the resulting displacement of the pile and communicating this to the computer; characterised in that:

v) the electronic computer is adapted to issue control signals to the jack in response to the measured magnitude of the test load so as to keep the test load substantially constant;

vi) the electronic computer is adapted to determine when a definite settlement rate for the pile has been attained and then to issue control signals to the jack so as to apply a new test load of different magnitude to the top of the pile in accordance with a predetermined regime of test loads; and vii) the electronic computer is adapted to repeat steps v) and vi) until the test regime is completed.

By providing computer control of the load testing procedure, together with automatic data logging, the present invention allows a much more detailed analysis of the structural integrity of the pile to be obtained. This analysis can be presented in real-time, advantageously in tabulated and/or graphic form, and reduces the risk of errors being introduced through manual processing of the data.

Furthermore, because the electronic computer receives data regarding the actual test load applied to the top of the pile, operating signals may be sent to the jack in order, for example, to maintain a given test load even when the pile is being displaced. This means that a given test load can be applied for a long period of time without the need for operating personnel to be present in order manually to adjust the applied load.

The computer can be arranged so as to control the jack to apply a number of different test loads to the pile, each for a predetermined minimum period of time or until a definite settlement rate has been achieved. In order to do this, the required load steps and intervals may be defined, together a specific settlement rate. The computer can then control the test load and make the required load changes as required. Load changes may be performed by successively increasing the applied load in small increments until the next desired substantially constant load level is achieved. If the settlement rate during the load change exceeds a predetermined maximum value, then the increase of the applied load may be paused until the settlement rate stabilises.

In preferred embodiments, the jack is a hydraulic jack controlled by the computer by way of a hydraulic control system. The applied test load may be calculated by monitoring the fluid pressure in the hydraulic control system driving the jack. This method, however, has the disadvantage that it is temperature sensitive (due to thermal expansion of the hydraulic fluid), and does not take into account friction between the jack and the point of contact on the top of the pile in the event that the test load is being applied eccentrically.

Accordingly, it is preferred to use one or more electronic load cells, which typically employ balanced strain gauges around a coaxial element. These may be placed above the jack on a spherical seating arrangement so as to reduce the risk of eccentric loading. Because the load cells measure the actual load applied to the pile, it is possible to operate the jack by way of the hydraulic control system so as to apply a substantially constant load, even when the pile is undergoing displacement. This feedback mechanism allows the applied load to be held constant to a degree hitherto not possible with manually-operated systems. The time interval between successive measurements of applied load and pile displacement can be of the order of a few seconds, say from 1 to 5 seconds. With the hydraulic control system set to adjust the hydraulic pressure applied to the jack in direct response to these measurements and on a similar timescale, a level of control previously unattainable is achieved, thereby greatly improving the quality of the testing results.

Advantageously, the computer is arranged so as to halt the testing process automatically, for example by stopping the flow of hydraulic fluid to the jack, when certain conditions are detected. This automatic fail-safe procedure is a further advantage over the known methods of static load-testing, and allows the present invention to be left unattended without undue risk. The fail-safe condition may be triggered in the following situations:

i) Where the magnitude of the applied test load reaches or exceeds a predetermined value. This may be, for example, the maximum tolerable by the reaction system or the maximum rating of the jack or the load cell.

ii) Where the magnitude of the applied test load drops by at least a predetermined amount, for example 10%, at a time when a constant load is to be maintained. This may be due to abrupt failure of the reaction system or failure of the foundation under test. Depletion of consumables such as hydraulic fluid and compressed air fail-safe intrinsically, and it is therefore not necessary to monitor their supply.

iii) Where the magnitude of the measured displacement of the pile reaches or exceeds a predetermined value, for example 10% of the pile diameter. This may be due to progressive failure of the pile, or excessive displacement of the pile head.

iv) Where the power supply to the computer falls to or below a predetermined level. If this happens, the test is discontinued and priority is given to the storage of data in a passive mode. In embodiments where a 12V battery is used as a power supply, the fail-safe condition may, for example, be triggered when the potential difference across the battery drops below 10V.

v) Where communication between the load measuring means and/or the displacement sensors and the computer is broken. This may happen as a result of electrical connections between the computer and the displacement sensors or the load cells being accidentally disconnected.

vi) In embodiments of the present invention in which two or more displacement sensors are disposed at different locations about the circumference of the pile, where the difference between the magnitudes of the displacements measured by the two or more displacement sensors reaches or exceeds a predetermined value, for example 50% of the average value recorded. This indicates that unwanted lateral loads are being applied to the pile, which in extreme cases can lead to structural damage or failure. This fail-safe also helps to detect misreadings from one or more of the displacement sensors.

Preferably, an additional displacement sensor is provided in order to detect any gradual upward movement of the reaction member, which is indicative of a gradual failure of the reaction system. This is because a gradual failure of this sort, which may be caused by an anchor pile being pulled from the ground, may still allow the load applied to the too of the pile to be maintained.

Alternatively or in addition, the ram extension of the jack may be monitored by measuring the volume of hydraulic fluid pumped to the jack by the hydraulic control system. This may be achieved by using a volumetric flowmeter, determining the level of hydraulic fluid in a reservoir of known size with a float or other means, or by any other suitable method. When the ram extension reaches or exceeds a predetermined value, this may be an indication of a failure in the reaction system or of a progressive failure in the pile, and a fail-safe signal is then generated so as to halt the testing process.

The area surrounding a pile test being undertaken in accordance with the present invention may be cordoned off with bunting, and a fine wire conductor system or trip wire may be installed so as to detect unauthorised access to the test site. The computer is advantageously configured so as to trigger the fail-safe condition in this event.

When the fail-safe condition is triggered, an alarm signal may be generated. This alarm signal may be transmitted to an operator or to a remote site by way of a mobile telephone or radio link, or by any other suitable method. Furthermore, data and control signals may be transmitted from and received by the computer so as to allow remote interrogation and control.

For a better understanding of the present invention, and to show how it may be carried into effect, reference shall now be made by way of example to the accompanying drawings, in which.

Figure 1:
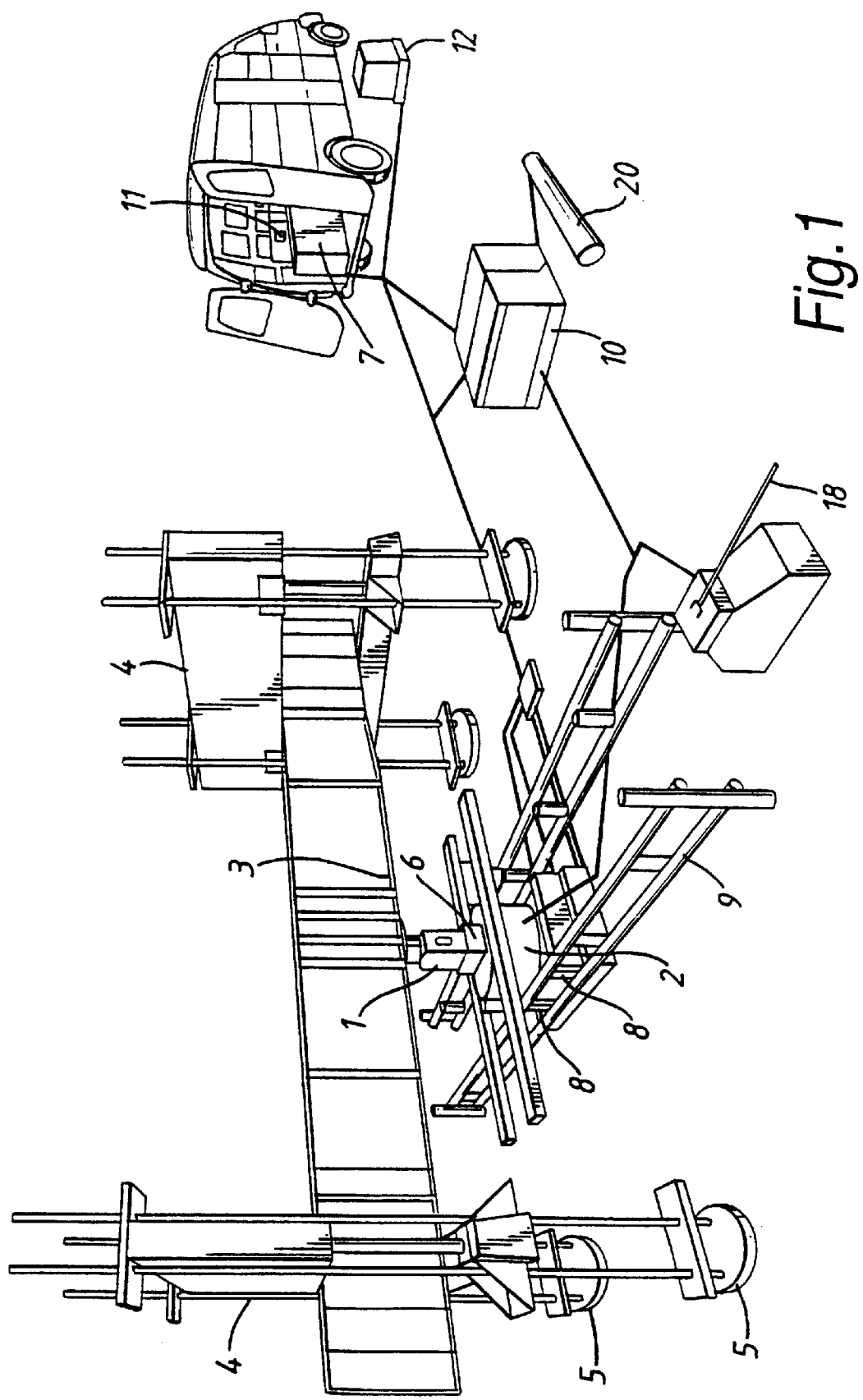
FIG. 1 shows the general configuration of a static load-testing rig.

FIG. 1 shows a static load testing rig suitable for use in the present invention. This rig comprises a jack 1 braced between the top of a pile 2 and a reaction member 3 The reaction member 3 is anchored to the ground by way of two support towers 4, each of which is firmly attached to the ground by way of one or more auxiliary piles 5. An electronic load cell 6 is mounted between the jack 1 and the top of the pile 2, and is connected to a data logger 7. Displacement sensors 8 are mounted around the pile 2 and are used to measure the displacement of the pile 2 relative to a reference frame 9. The displacement sensors 8 are also connected to the data logger 7. A hydraulic control system 10, which will be described hereinafter in more detail, serves to control the jack 1. Both the data logger 7 and the hydraulic control system 10 are operatively linked to a host computer 11.

The data logger 7 may be a "CR10", which is a data logging computer available from Campbell Scientific and often used, for example, in weather balloons. The data logger 7 can readily be programmed to regulate all the functions, measuring the displacement sensors 8 at intervals of, for example, 2.5 seconds and recording the data at chosen intervals. It also checks the load applied to the pile 2 at each interval and effects any change required to the applied load by controlling the hydraulic pressure feeding the jack 1. The data logger 7 may also be programmed to check the safe progress of the test and to control all of the load changes required.

The measurement monitoring and control is carried out by a suitably programmed CR10 data logger 7, which is battery-powered and can store up to 30,000 data values. The acquisition and processing functions are controlled by user-entered instructions in program form which are downloaded via a standard RS232 communications data link from a host PC (Personal Computer) 11 which acts also as a display terminal to view the actual data being monitored by the data logger 7. The PC 11 can also receive and store the last data recorded by the data logger 7 so that it remains updated and does not require the transfer of all the data every time a connection is made. The host PC 11 acts as a display terminal while all the control and measurement functions are performed by the data logger 7 itself. The data communications link can also be over a modem or digital mobile radio or telephone ink.

Among the in-built functions of the data logger 7 is a four-wire full bridge measurement facility with temperature compensation, which is employed to monitor the load cell 6. The standard analogue input channels are used for the measurement of the displacement sensors 8. For these measurements a resolution of 333 $\mu$V on the selected full scale range of 2.5V is quoted. For an ideal displacement sensor of 100 mm travel, this equates to a resolution of 0.013 mm.

Two selector switches (not shown) can be connected to the digital channels allowing manual selection of the operation mode from: i) standby, ii) datum, iii) reading and iv) logging; and selection of the interval of data logging from: i) 10 seconds, ii) 1 minute, iii) 5 minutes and iv) 10 minutes.

The operation mode allows program flow control to provide storage of the datum values so that subsequent readings take any offsets into account directly.

A ten turn potentiometer (not shown) is provided on the front panel with a digital readout which provides for manual input to the data logger 7 of the desired load. Exact calibration of this variable resistance is not found necessary as the interpreted desired load is displayed directly on the screen of the PC 11. A facility in the control software is also included to lock off any further subsequent readings of this potentiometer, since it is found that the chosen desired load is not always as constant as might be expected: once this facility is included in the program, the parameter location can be made directly accessible from the host PC 11 and can be changed precisely. The potentiometer can be retained as a back-up solution.

A data set is programmed to consist of date and time, the readings of the displacement sensors 8 and the actual load measured together with the desired a load.

The power for the data logger 7 is derived from an uninterruptable power supply (not shown) which is arranged with a 16 A/h battery back-up, which gives a minimum of five days continuous logging on a fully-charged battery. Because the operation of the system can be practically continuous, portable generators 12 may be used to provide the mains power for the host PC 11 and simultaneously to charge the battery when possible.

Figure 2:
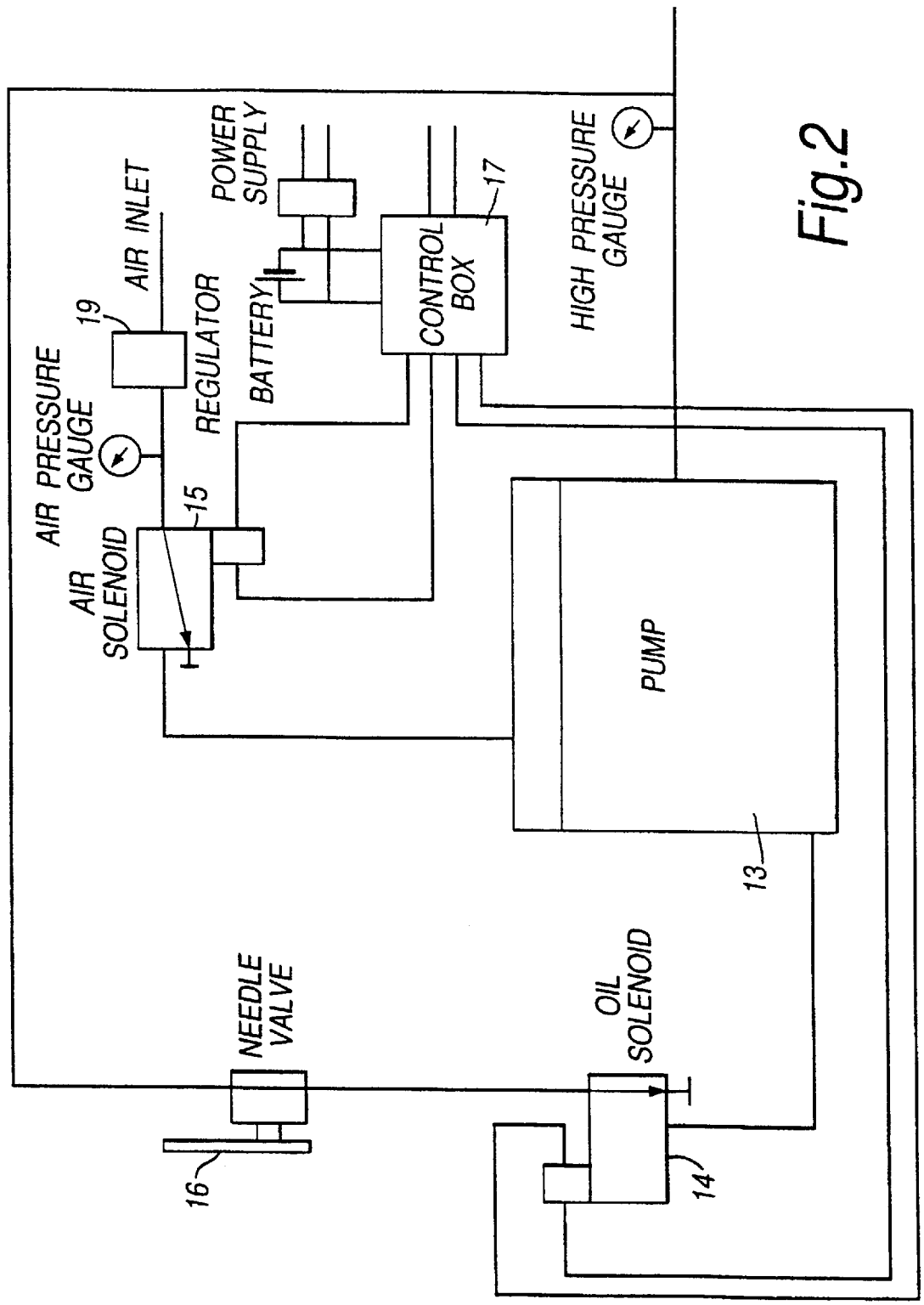
FIG. 2 shows a hydraulic control system for use with the present invention.

A further feature of the CR10 data logger 7 is that it can be programmed to control several output ports which are conveniently arranged to operate the hydraulic control system 10 which includes a pneumatic to hydraulic pump 13 to increase applied load and to operate an oil solenoid 14 to allow the jack pressure to be decreased as required. The output from the appropriate data logger channels are employed to drive MOSFETs (metal-oxide semiconductor field effect transistors) which switch the respective solenoids 14, 15 in the hydraulic control system 10, which is shown in more detail in FIG. 2.

The components illustrated are housed separately from the data logger 7, with its own battery charger. A gas solenoid 15 primes the hydraulic pump 13 from a 100 psi (689 kPa) supply. This gas supply may be generated from an air compressor (not shown) or more conveniently from a gas bottle 20. The preferred choice is the use of gas bottles filled with oxygen-free nitrogen. This gas is dry, minimising condensation and subsequent freezing inside the pump relief valve which can impede its correct operation in cold weather.

The electronically-controlled release of hydraulic pressure uses a high pressure oil solenoid 14 through a needle valve 16 to control the rate of discharge. The connections to the data logger 7, by way of a control box 17, provide a-switched return path for operation of the solenoids 14, 15.

The load application to the head of the pile 2 is carried out by the use of a hydraulic jack 1; hydraulic pressure is produced by use of a suitable pump 13, 18. For most pile test applications a manually-operated hand pump 18 is adequate for coarse load control. This aspect of the conventional test arrangement may be retained for two principal reasons: i) the manual pump 18 may be used to allow the jack 1 to take up any slack between the load cell 6 and the reaction frame 3, and ii) in the unlikely event of failure of the automatic load control system, the test can be continued manually.

If manual load control is attempted, it is generally found that if the load is measured using a hydraulic pressure gauge, which can only be resolved to the nearest 1%, the actual resultant load control is unlikely to be better than approximately 2%. In contrast, employing an electronic load cell 6 and a computerised load maintaining arrangement 10, it can be arranged so that the relative magnitude of load applied is checked every few seconds and a suitable correction made to the applied load if the deviation is greater than an arbitrary figure, say 5 kN. It should be noted that reliance may be placed on the resolution of the load measuring system to maintain the applied load constant to within 0.2% for most typical tests loads.

A Maximator® "S"-type air-driven hydraulic pump 13 may be used in the automatic load control system 10. This pump works on a differential area piston principle, applying air to the large surface area of the air drive piston (not shown) which is mechanically connected to a smaller hydraulic piston (not shown). This converts pneumatic energy into hydraulic power. Automatic changeover of pistons is achieved by a pilot valve triggered by a servo slide valve (not shown). This valve has no pressure balance control, therefore eliminating stalling during normal operation. The pump 13 cycles more slowly as it approaches the specified maximum pressure and stops, when hydraulic and air pressure forces are in balance. The pump 13 then maintains the specified pressure output without further intervention or energy consumption.

The magnitude of any load correction required may be determined within the data logger 7 every 2.5 seconds; this is then translated into timing signals which are made to operate an increase or a decrease of the hydraulic pressure. A scaling factor is employed to make the system sufficiently versatile to accommodate varying sizes of jack 1 and perform successfully the two principal functions: a) maintain the load within tight boundaries, and b) change the load when required.

Figure 3:
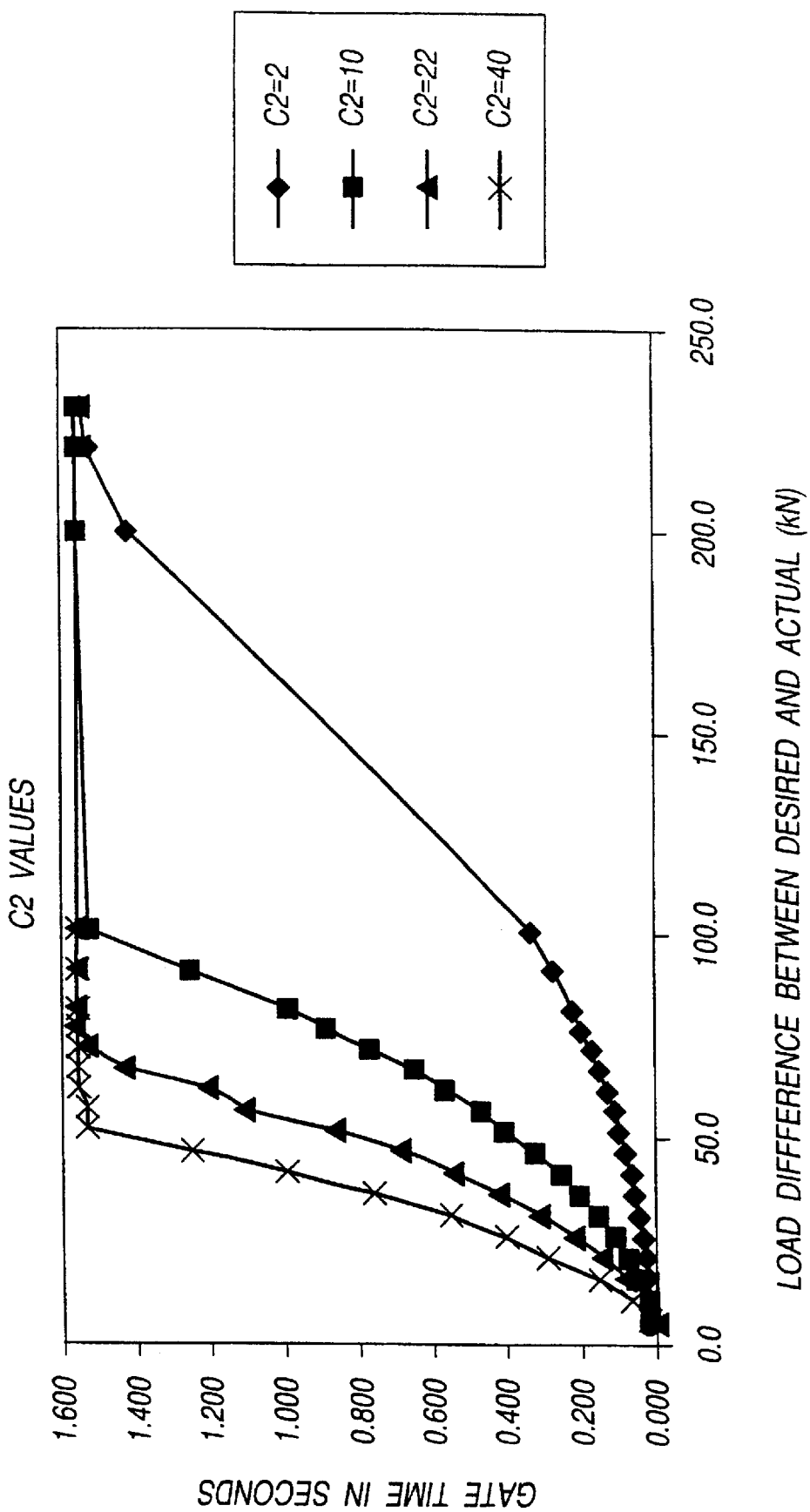
FIG. 3 is a graph illustrating a control algorithm used by the hydraulic control system of FIG. 2.

A simple control algorithm may be employed to determine the duration of a control pulse which opens a pneumatic valve 19 for a predetermined period which should correspond to the load change required. The timing interval is derived from an equation of the form $t_p = C0 + C2 x^2$ where x is the difference between applied load and desired load; for most typical jacks 1 in the 3000 kN to 10000 kN range, the optimum C2 value is 22, and C0 remains constant at 1.5. FIG. 3 indicates the resultant variation with this coefficient on the pulse applied to the control switches of the hydraulic control system 10.

When changing loads, the operation of the timing circuits is usually limited to a maximum of approximately 1.5 seconds. It is usually less than the 2.5 seconds program cycle to ensure correct operation of the software.

A significant bonus in introducing a computerised hydraulic control system 10 is that the load applied can be held truly constant within tight controllable limits. As a consequence, the displacement in time of the foundation system under test is not distorted by induced load variations.

Many suitable electronic displacement sensors 8 are commercially available, allowing total displacements of up to 250 mm to be measured with excellent resolution. The currently preferred and most reliable sensors 8 are resistive elements which employ a carbon strip such as those from Penny & Giles (typical ref: HLP190/FS1/100/4k).

A modification required on some of the sensors is the installation of a return spring (not shown) to ensure that the travel of the arm of the sensor is sprung loaded to its fully-extended position; Penny & Giles offer a sprung-loaded sensor. The sensor 8 also requires the installation of a suitable mounting arrangement which allows the gauges to be secured and rapidly attached to the reference frame 9.

Calibration of the displacement sensors 8 is also desirable to ensure that constancy between different sensors 8 is maintained. This calibration may be carried out against a digital vernier calliper; it should be noted that one of the largest inaccuracies encountered during calibration is the verticality of the gauge with respect to the reference standard. This only becomes significant when high accuracy is being sought as repeatability of measurement with just a 0.10 variation, which represents less than 1:1000, can be equated to a variation of displacement of 0.1%. This inaccuracy with verticality of the gauge is also applicable to measurement of pile head movement.

What is claimed is:

1. A method for testing the static load-bearing capacity of a pile, wherein:
   i) a test load is supplied to the top of the pile by way of a jack braced against a reaction member, thereby causing a resultant displacement of the pile;
   ii) the magnitude of the load is determined by measuring means and communicated to an electronic computer;
   iii) the resultant displacement of the pile is measured by at least one displacement sensor and communicated to said electronic computer; characterized in that:
   iv) the electronic computer issues control signals to the jack in response to the measured magnitude of the test load so as to keep the test load substantially constant;
   v) the electronic computer operates in response to displacement values measured by the at least one displacement sensor to determine when a definite settlement rate for the pile has been attained and then issues control signals to the jack so as to apply a new test load of different magnitude to the top of the pile in accordance with a predetermined test regime of test loads, the regime being composed of a given plurality of different test loads sufficient to fully test the static load-bearing capacity of the pile; and
   vi) steps ii) to v) are repeated until the test regime is completed.

2. A method according to claim 1, wherein an additional displacement sensor is provided so as to measure upward movement of the reaction member and wherein a fail-safe signal is triggered to stop the static load-bearing test when the electronic computer determines that the rate of said upward movement reaches or exceeds a predetermined value.

3. A method according to claim 1, wherein the magnitude of the test load is determined by an electronic load cell.

4. A method according to claim 1, wherein a fail-safe signal is triggered to stop the static load-bearing test when the electronic computer determines the occurrence of one or more of the following conditions:
   a) the magnitude of the applied test load reaches or exceeds a predetermined value;
   b) the magnitude of the applied test load drops by at least a predetermined amount;
   c) the magnitude of the measured displacement of the pile reaches or exceeds a predetermined value;
   d) a power supply to said computer falls to or below a predetermined level;
   e) the communication between the load measuring means and/or the displacement sensors and the computer is broken.

5. A method according to claim 1, wherein two or more displacement sensors are disposed at different locations about the circumference of the pile, and wherein a fail-safe signal is triggered to stop the static load-bearing test when the electronic computer determines that the difference between the magnitudes of the displacements measured by the displacement sensors reaches or exceeds a predetermined value.

6. A method according to claim 1, wherein a fail-safe signal is triggered to stop the static load-bearing test when the electronic computer determines that the volume of hydraulic fluid supplied to the jack reaches or exceeds a predetermined value.

7. A method according to claim 2, wherein an alarm signal is generated in the event of the fail-safe signal being triggered.

8. A method according to claim 7, wherein the alarm signal is transmitted to a remote location by way of a telecommunications link.

9. An apparatus for testing the static load-bearing capacity of a pile, the apparatus comprising:
   i) an electronic computer with a power supply;
   ii) a jack, which in use is braced between the pile and a reaction member so as to apply a test load to the top of the pile, thereby causing a resultant displacement of the pile;
   ii) means for measuring the magnitude of the test load and communicating this to the computer;
   iv) at least one displacement sensor for measuring the resultant displacement of the pile and communicating this to the computer; characterized in that:

v) the electronic computer is adapted to issue control signals to the jack in response to the measured magnitude of the test load so as to keep the test load substantially constant;

vi) the electronic computer is operated in response to displacement values measured by the at least one displacement sensor to determine when a definite settlement rate for the pile has been attained and then to issue control signals to the jack so as to apply a new test load of different magnitude to the pile in accordance with a predetermined test regime of test loads, the regime being composed of a given plurality of different test loads sufficient to fully test the static load-bearing capacity of the pile; and vii) the electronic computer is adapted to repeat steps v) and vi) until the test regime is completed.

10. A apparatus as claimed in claim 9, comprising an additional displacement sensor for measuring upward movement of the reaction member and wherein a fail-safe signal is triggered to stop the static load-bearing test when the electronic computer determines that the rate of said upward movement reaches or exceeds a predetermined value.

11. An apparatus as claimed in claim 9 or 10, wherein the means for measuring the applied test load is an electronic load cell.

12. An apparatus as claimed in claim 9, comprising means for triggering a fail-safe signal to stop the static load-bearing test when the electronic computer determines the occurrence of one or more of the following conditions:

a) the magnitude of the applied test load reaches or exceeds a predetermined value;

b) the magnitude of the applied test load drops by at least a predetermined amount;

c) the magnitude of the measured displacement of the pile reaches or exceeds a predetermined value;

d) a power supply to said computer falls to or below a predetermined level;

e) the communication between the load measuring means and/or the displacement sensors and the computer is broken.

13. An apparatus as claimed in claim 9, comprising two or more displacement sensors disposed at different locations about the circumference of the pile, and wherein a fail-safe signal is triggered to stop the static load-bearing test when the electronic computer determines that the difference between the magnitudes of the displacements measured by the displacement sensors reaches or exceeds a predetermined value.

14. An apparatus as claimed in claim 9, comprising means for measuring the volume of hydraulic fluid supplied to the jack and wherein a fail-safe signal is triggered to stop the static load-bearing test when the electronic computer determines that the said volume reaches or exceeds a predetermined value.

15. An apparatus as claimed in claim 10, comprising means for generating an alarm signal in the event of the fail-safe signal being triggered.

16. A method according to claim 15, comprising telecommunications means for transmitting the alarm signal to a remote location.

* * * * *